United States Patent [19]

Islava

[11] Patent Number: 5,788,658
[45] Date of Patent: Aug. 4, 1998

[54] FIELD ADJUSTABLE EXTRICATION COLLAR

[76] Inventor: Steven T. Islava, 315 Marigold, Corona del Mar, Calif. 92625

[21] Appl. No.: 792,106

[22] Filed: Jan. 31, 1997

[51] Int. Cl.[6] .................................................. A61F 5/00
[52] U.S. Cl. .................................................. 602/18; 602/6
[58] Field of Search ........................ 602/5–8, 15, 17–19

[56] References Cited

U.S. PATENT DOCUMENTS

| | | | |
|---|---|---|---|
| 3,320,950 | 5/1967 | McElvenny | 602/18 |
| 3,512,523 | 5/1970 | Barnett | 602/18 |
| 3,916,884 | 11/1975 | Attenburrow | 602/18 |
| 4,232,663 | 11/1980 | Newton | 602/18 |
| 4,383,526 | 5/1983 | Robins | 602/15 |
| 4,712,540 | 12/1987 | Tucker et al. | 602/18 |
| 4,966,136 | 10/1990 | Bates | 602/18 |
| 5,158,531 | 10/1992 | Zamosky | 602/5 X |

*Primary Examiner*—Linda C. Dvorak
*Attorney, Agent, or Firm*—Graham & James

[57] ABSTRACT

An extrication collar for immobilizing the head and neck of an injured victim is field adjustable by an emergency medical technician who matches the size of the victim by tearing lower and/or upper peripheral portions of the extrication collar off along a perforated line. The vertical height of the collar and hence the length of neck to which the collar is adjusted is varied by the amount of the collar periphery, which is removed by manually tearing along a perforated line. The plurality of perforated lines are defined through the collar to provide a plurality of discrete sizes. Rigidity of the collar is provided by an exterior and noncompressible foam layer, while cushioning of the collar is provided by an interior compressible foam bonded to the noncompressible foam. The noncompressible foam or the compressible foam or both are selectively separable through the perforated lines in the front portion of the collar, the back portion of the collar or both.

22 Claims, 4 Drawing Sheets

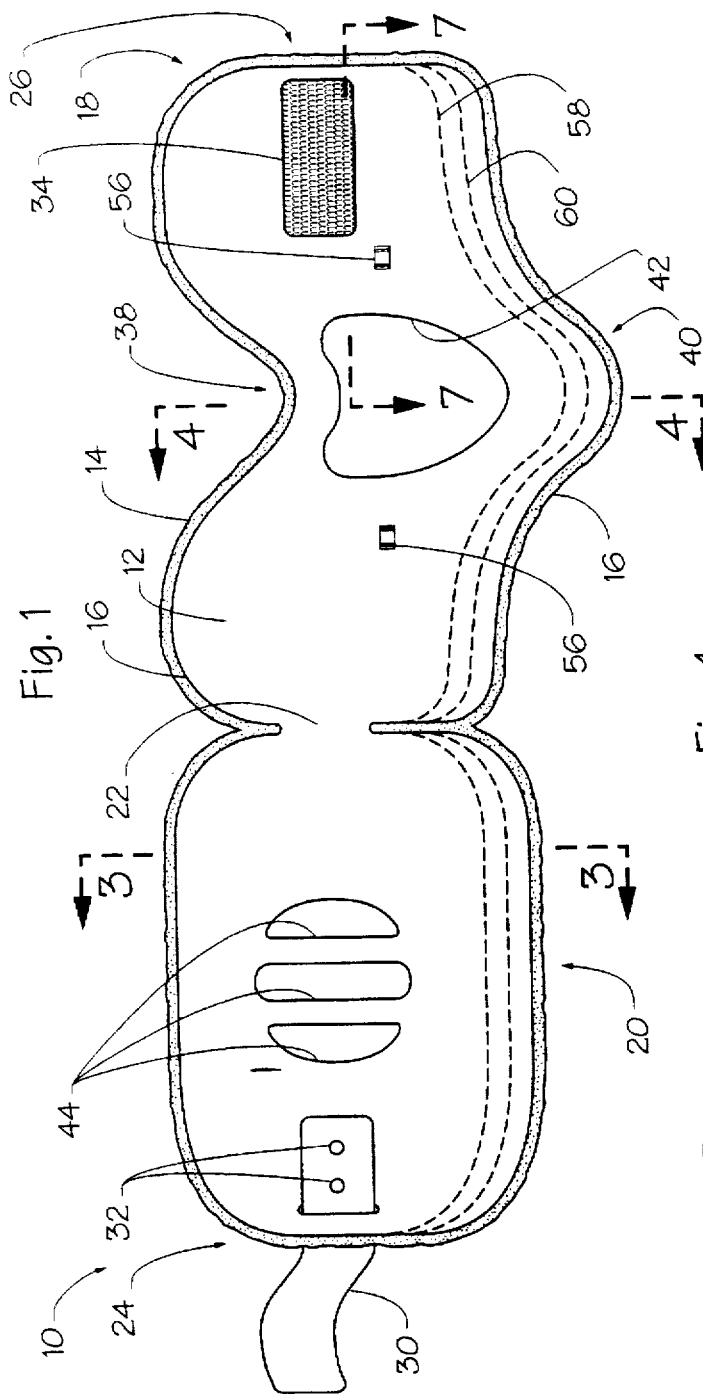
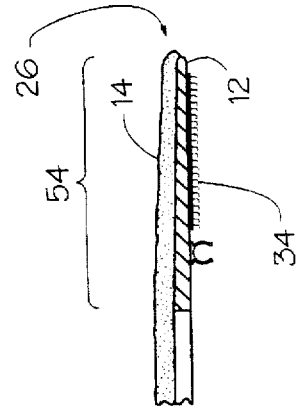
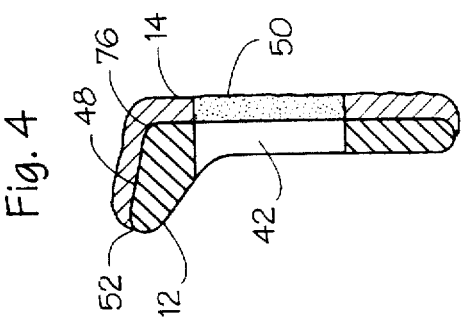
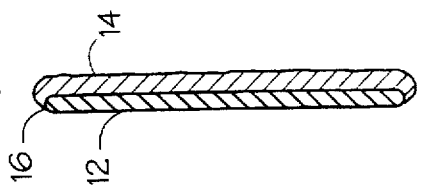

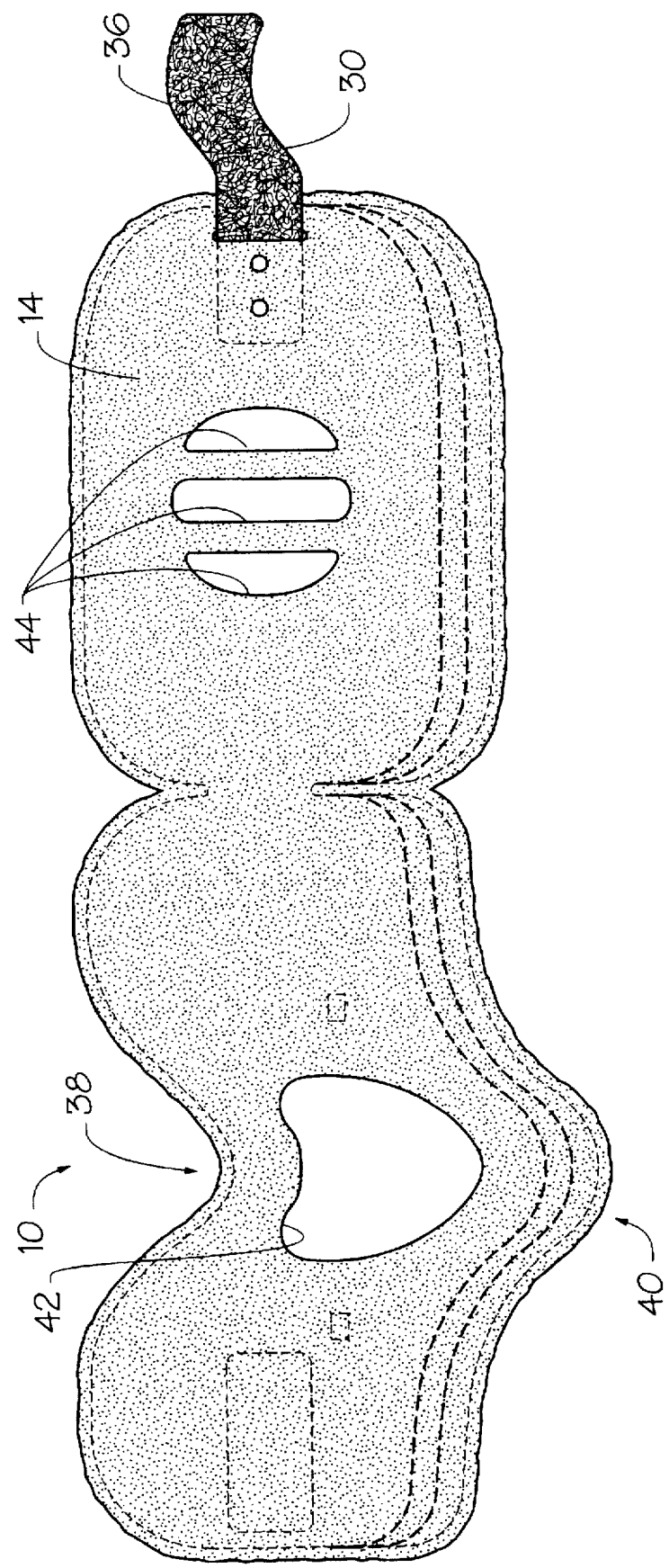

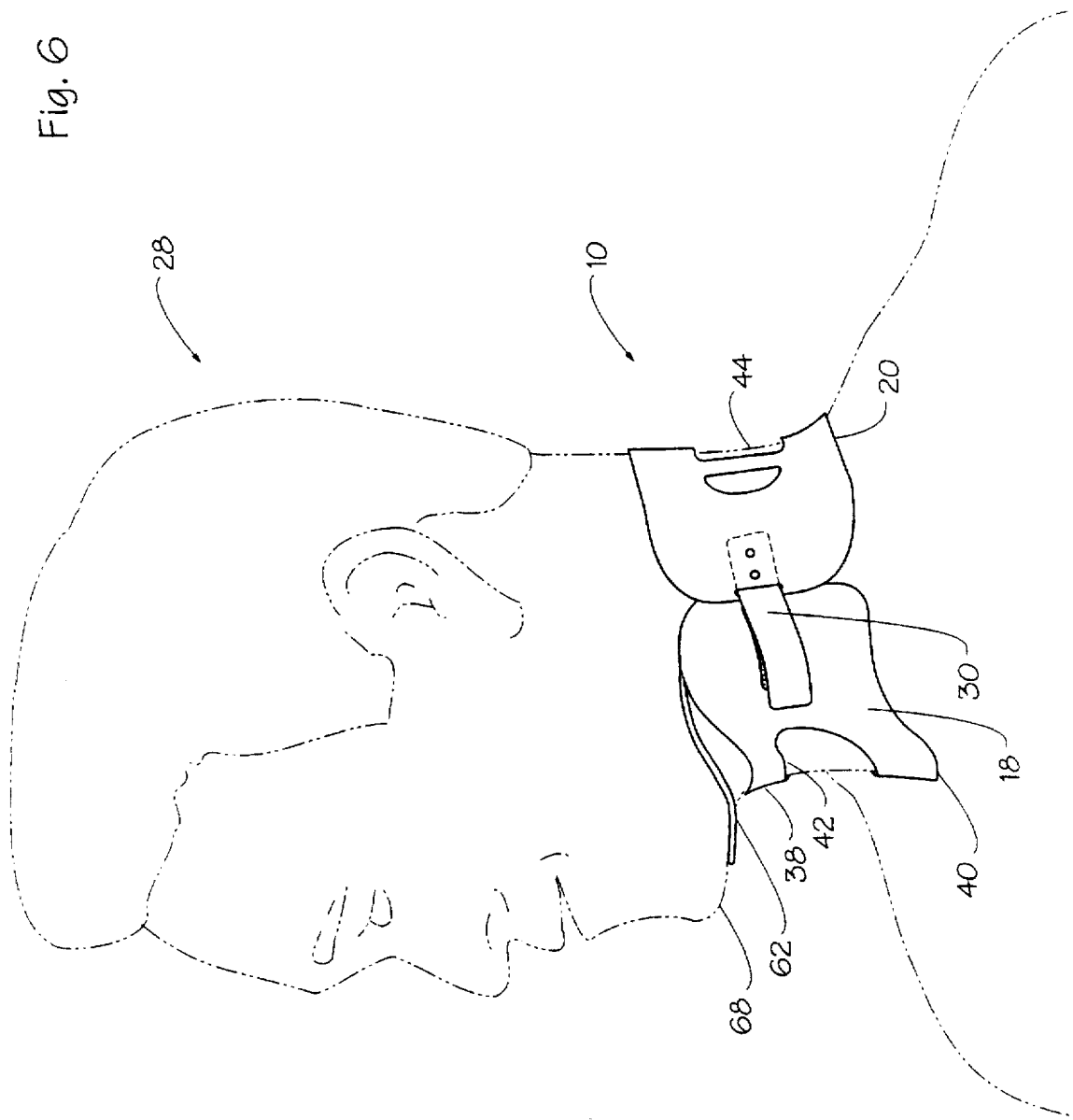

FIELD ADJUSTABLE EXTRICATION COLLAR

BACKGROUND OF THE INVENTION

1. Field of the Invention

The invention relates to the field of cervical collars intended to be fitted to persons with neck or spinal injuries, and more particularly to a cervical extrication collar which can be adjusted in the field to fit injury victims of different size.

2. Description of Prior Art

Cervical support collars or neck braces are well known for the purpose of immobilizing the head and neck during the convalescence or transport of a person with a spinal injury. It is also generally appreciated that bone to jaw distance of a collar varies from person to person. To obtain proper immobilization or support it is necessary to have an appropriate physical support between the shoulders and upper chest to the jaw and skull for the entire length of the upper spinal column. Therefore, one size of neck collar does not fit all persons. In addition adult sizes will not likely fit children.

To accommodate each differently sized user various designs have been contemplated in the prior art including designs which had to be cut to shape as shown by McElvenny, "Neck Brace," U.S. Pat. No. 3,320,950 (1967).

Another option was to provide cervical support collars which were foldable in some manner for the purpose of size adjustment such as shown by Attenburrow, "Supporting Collar," U.S. Pat. No. 3,916,884 (1975); and Christensen, "Multi-purpose Wilderness Splint," U.S. Pat. No. 5,336,160 (1994).

The most common solution applied by the prior art was to provide designs which had telescopic parts which were selectively clamped together by some means such as shown by Martin, "Adjustable Cervical Collar," U.S. Pat. No. 5,520,619 (1996); Gorsen, "Spring Loaded Cervical Collar," U.S. Pat. No. 4,827,915 (1989), Alderson, "Cervical Traction Collar," U.S. Pat. No. 3,364,926 (1968), Gaylord, Jr., "Adjustable Cervical Collar," U.S. Pat. No. 3,916,885 (1975); Barnett, "Cervical Collar with Means for Varying the Height and Shape Thereof," U.S. Pat. No. 3,512,523 (1970); and Monfardini, "Single Piece Adjustable Cervical Collar," U.S. Pat. No. 3,024,784 (1962).

Other designs simply appear to contemplate collars which were bendable to fit such as Schmid, et al., "Disposable Cervical Collar," U.S. Pat. No. 5,060,637 (1991); and Garth, "Portable Cervical Collar," Reissue 32,219 (1986).

Finally, the prior art designs have also included supports that include some type of an inflatable element for providing rigidity in selected portions while allowing bendability in others. See Curlee, "Compound Force Therapeutic Corset," U.S. Pat. No. 4,682,588 (1987).

All of these cervical collars or supports suffer from one or more disadvantages either in terms of complexity, cost, comfort, rigidity, reusability or ease of use. The aspect of cost becomes a particularly important factor with extrication collars, which are used by emergency paramedics in the field. These collars must generally be disposable, since the emergency medical technician (EMT) in most cases will not obtain the return of any cervical collar from the receiving hospital where the injury victim is delivered. Therefore, the most costly and complex telescopic adjustable collars are not economically practicable for field use by EMTs. As a result, the prior art practice of EMTs throughout the United States has been to stock three sizes of low cost, disposable collars in their emergency vehicles. The problem, of course, is maintain an adequate inventory on a day-to-day basis within the emergency vehicle. Should the emergency medical personnel be required to service an accident site in which there are a plurality of victims or to service multiple sites in short consecutive periods, it is highly likely that he or she will fail to have a sufficient number of collars in inventory of each of the needed sizes and in the numbers required. As a result, EMTs have often been forced to use collars which are slightly too large or too small for the accident victim, thereby forfeiting in some cases part or all of the benefits which the extrication collar is intended to provide the victim.

Therefore, what is needed in an extrication collar which is not subject to the foregoing defects and which can be economically manufactured and fitted to patients of all sizes without the necessity of carrying a large inventory.

BRIEF SUMMARY OF THE INVENTION

The invention is a cervical collar comprising a body adapted for being wrapped around a user's neck and providing for immobilization of the neck and/or head. At least one perforated line is defined at least part way through the body, which renders at least part of the body manually separable from the body without the use of a tool. The separable portion is defined along at least a portion of the body so that separation of the portion effects a change in size of the body insofar as structural support for immobilization of the neck is concerned. As a result, a single cervical collar made be adapted to users of different sizes.

The body is comprised of a first substantially non-compressible flexible layer and a second compressible flexible layer affixed thereto. The first layer provides structural support, and the second layer provides cushioning for the user. The first layer is comprised of 10 lb cross-linked polyethylene foam and the second layer comprised of 2 lb cross-linked polyethylene foam.

The body has an upper peripheral edge and a lower peripheral edge. In one embodiment the perforated line is defined adjacent to the lower peripheral edge, but in another it is defined adjacent to the upper peripheral edge, or both. A plurality of perforated lines may be defined through the body. Each perforated line defines a size of the body for the different size of user. The perforated line is at least partially defined through the first layer, or may be completely defined through the first layer. The perforated line may also be partially defined through the second layer or completely defined through the second layer. The perforated line may be continuous or discontinuous. The second layer may or may not be affixed to the first layer between the closest one of the upper and lower peripheries and at least one perforated line.

In a second embodiment the body further comprises a jaw support extending from the body. The jaw support is a jaw loop integrally connected to the body and hinged thereto.

The invention may now be better visualized by turning to the following drawings where like elements are referenced by like numerals.

BRIEF DESCRIPTION OF THE DRAWING

FIG. 1 is an outside plan view of the exterior surface of an extrication collar devised according to the invention with the collar laid flatly to show its outline.

FIG. 2 is the inside plan view of the interior surface of the extrication collar of FIG. 1 as seen when the collar is laid out flatly.

FIG. 3 is a cross-sectional view taken through section lines 3—3 of FIG. 1.

FIG. 4 is a cross-sectional view taken through section line 4—4 of FIG. 1.

FIG. 6 is a perspective view of the collar of FIG. 5 shown fitted to a user.

FIG. 7 is an alternate cross-sectional view in accordance with the invention.

Figure 5:
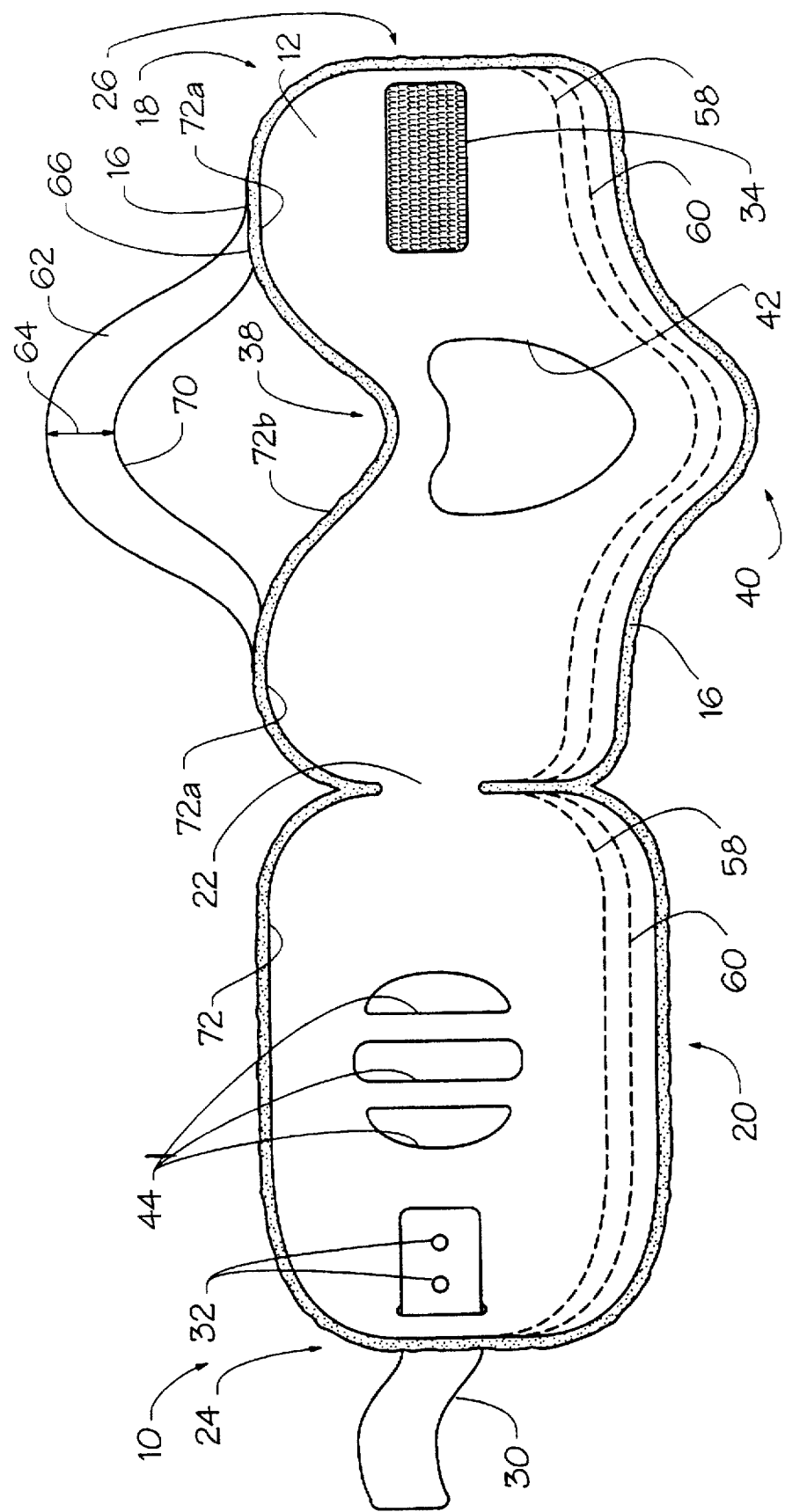
FIG. 5 is a plan view of the exterior surface of a second embodiment of the extrication collar incorporating the invention.

The invention now having been briefly summarized and illustrated, the various embodiments can now be better understood by turning to the following detailed description.

DETAILED DESCRIPTION OF THE PREFERRED EMBODIMENTS

An extrication collar for immobilizing the head and neck of an injured victim is adjustable for size of the victim in the field by an emergency medical technical by means of a shape and size reduction of the extrication collar by tearing the lower and/or upper peripheral portions of the extrication collar off along a perforated line. The vertical height of the collar and hence the length of neck to which the collar is adjusted is varied by the amount of the collar periphery, which is removed by manually tearing along a perforated line. The plurality of perforated lines are defined through the collar to provide a plurality of discrete sizes. Rigidity of the collar is provided by an exterior and noncompressible foam layer, while cushioning of the collar is provided by an interior compressible foam bonded to the noncompressible foam. The noncompressible foam or the compressible foam or both are selectively separable through the perforated lines in the front portion of the collar, the back portion of the collar or both.

FIG. 1 is an outside or exterior elevational view of extrication collar 10 of the invention as would be seen if collar 10 were laid out flatly in a plane. Collar 10 is comprised of two layers of material, a first layer 12 composed of a first substantially noncompressible, but bendable foam which is the primary surface illustrated in the plan view of FIG. 1 and affixed, adhered or bonded thereto on its backside, a second soft compressible foam layer 14 shown in FIG. 1. Soft layer 14 is shown as extending beyond peripheral edge 16 of layer 12 for purposes of comfort and forming the primary inner surface as depicted in the plan elevational view of FIG. 2. FIG. 2 is a plan elevational view of collar 10 laid out flatly, but flipped over or reversed from the orientation shown in FIG. 1.

For example in the presently illustrated embodiment, noncompressible foam layer 12 is approximately ¼ inch thick and is composed of 10 lb cross-linked polyethylene foam such as manufactured by Pal Foam of Costa Mesa, Calif. under the catalogue number 900. While referenced here as a noncompressible foam layer 12, layer 12 expressly is meant to include materials that have a limited or measured amount of noncompressibility or conversely compressibility, and which includes materials, which may not in fact be "foam". Layer 12 need only be a bendable and resilient material which provides adequate structural support for neck and head immobilization. Layer 12 need not be rigid for this characteristic to be satisfied. Similarly, compressible foam 14 in the illustrated embodiment is ⅛ inch thick and is composed of 2 lb cross-linked polyethylene foam such as manufactured by Pal Foam of Costa Mesa, Calif. under the catalogue number 900. Any material whether it be foam or compressible which provides padding and comfort may be substituted. It is to be expressly understood that many other types of material may be employed than those specifically described while still being consistent with the scope of the present invention. Compressible foam layer 14 provides for a comfortable fitting as its primary purpose while substantially non-compressible foam layer 12 provides for structural support and shape as its primary purpose.

It is also possible to omit compressible foam layer 14 if desired or to combine the two functions of layers 12 and 14 in a single layer of material having intermediate physical characteristics between the two separate layers 12 and 14 illustrated here.

Collar 10 in the illustrated embodiment includes a front neck portion generally denoted by reference numeral 18 and a back neck portion generally denoted by reference numeral 20. Front neck portion 18 and back neck portion 20 are integrally joined together through a necked down hinge region 22 defined in layer 12. A nonintegral coupling between portions 18 and 20 is also contemplated. While layer 12 both in front portion 18 and rear portion 20 is bendable, resilient and curved at the neck as illustrated in FIG. 6, necked down portion 22 facilitates easier bending at the side of the neck. Instead of a necked down portion 22, a thinned or slotted portion may be substituted to give a greater degree of flexibility to bending around the neck at this point in collar 10.

Opposing exterior edge 24 of back portion 20 and exterior edge 26 of front portion 18 are at opposite ends of collar 10, when collar 10 is laid flatly. When collar is folded into a generally cylindrical shape for fitting to an injury victim 28 as shown in FIG. 6, edge 24 is coupled to edge 26 or more properly the left edge portion 24 of back portion 20 and the right edge portion 26 of front portion 18 are coupled together by means of a temporary fastener. In the illustrated embodiment the fastener is comprised of a Velcro fastener including a strap 30 permanently coupled to back portion 20 by means of screws or rivets 32 and a coupling patch 34 on front portion 18. All or part of the back surface 36 of strap 30 as shown in FIG. 2 are provided with Velcro hooks or their equivalent, while all or a substantial portion of exposed surface of patch 34 are provided with Velcro eyes. The arrangement of hooks and eyes could be reversed if desired. Patch 34 is attached to front portion 18 by means of bonding, adhesive, or other permanent means.

Collar 10 includes an exterior periphery 16, which is shaped in order to comfortably fit victim 28 as well as to provide structural support or immobilization of the neck and head. Periphery 16 is contoured to fit the appropriate sections of the human form and may be varied according to the size or shape of victim 28 which collar 10 is intended to fit as described below. For example, in the embodiment of FIG. 1 a chin indentation 38 is provided in front portion 18 along the top edge periphery 16 while a corresponding and opposing chin protrusion 40 is provided in the lower periphery 16 of front portion 18. This provides effective chin support without choking according to the external morphology of the human body. Similar, back portion 20 is a generally a rounded rectangle to provide the required rear neck and head support characteristic of the human morphology at the back of the neck and head.

Front portion 18 may also have a heart shaped opening 42 defined through both layers 12 and 14 to provide tracheal access to victim 28 for tracheotomies and other procedures while collar 10 is fitted to the victim. Rear portion 20 similarly has a plurality of vent holes 44 defined through layers 12 and 14 to provide for cooling ventilation and free perspiration. The shape and placement of vent holes 44 can be widely varied as long as the configuration does not significantly weaken the vertical structural support provided by back portion 20. In the illustrated embodiment a generally circular vent hole with cords of the circle provided with integrally extending ribs effectively serve the purpose of ventilation without compromising vertical structural integrity.

FIG. 3 is a cross-sectional view taken through section lines 3—3 of FIG. 1 and shows soft compressible foam layer 14 in the inside surface of substantially noncompressible structural foam layer 12. Foam layer 14 is molded onto the rear surface of foam layer 12 and hence tends to fold, flow over or encapsulate peripheral edges 16 of foam layer 12 thereby providing additional measure of comfort and protection against the harder edge of layer 12.

In the case of front portion 18 as seen through the mid-line cross-sectional view taken through section lines 4—4 and as depicted in FIG. 4, foam layer 12 includes a thickened and cantilevered chin support 46. Chin support 46 may be either integrally molded with front portion 18 or may be separately molded and attached thereto by adhesive, bonding or other permanent means to provide an inclined supporting surface 48 for the lower jaw. Soft foam layer 14 is bonded to surface 48 continuing from the rear surface 50 of layer 12 to the front edge 52 of chin support 46.

In one embodiment, outer edge portions 24 and 26 of front portion 18 and 20 respectively may be thinned in their thickness as shown in FIG. 7 which is a cross-sectional view taken through section lines 7—7 of FIG. 1. As shown in FIG. 7 a tapered portion 54 may be provided in which the thickness of either or both foam layers 12 and 14 are gradually reduced as edge 26 is approached. Thus, when opposing edge 24 is overlapped with edge 26, instead of obtaining a doubling of the thickness of collar 10, a reduced and more gradual thickness from any overlap is provided.

Finally, in the illustrated embodiment of FIG. 1 collar 10 may be provided with one or more nasal canula clips 56. Any clip or attachment means now or later devised may be employed instead of the tubal clips 56 illustrated. Clips 56 are used to allow a nasal canula tube to be temporarily attached to collar 10 when collar 10 is applied to victim 28. Typically a canula, which is not shown, would be led through clip 56 upwardly over the patient's ear and then down through and inserted into the nostrils. Typically, administration of oxygen is supplied in this means to a victim who may be under respiratory stress.

The overall shape and function of collar 10 now having been described, consider in more the means for providing size adjustment. Lines of perforation 58 and 60 illustrated in the embodiment of FIG. 1 and 2. Foam layer 12 and preferably foam layer 14 are both perforated with a plurality of slits, slots, dots or other openings along a contoured line adjacent to the bottom or top periphery 16 or both of collar 10. The openings define perforated lines 58 and 60 in collar 10 may be defined partially or entirely through layer 12 and partially or entirely through layer 14. The shape of perforated lines 58 and 60 are chosen again to match the outward morphology of the human shape and hence are typically parallel to or shaped similarly to the exterior peripheral edges 16. The shape of the contour may be varied as dictated by size.

The size of the perforations which define lines 58 and 60 are such when in combination with the strength or tear resistance of foam layers 12 and/or 14, the EMT can grasp a portion of the edge of collar 10 and manually tear along either perforated lines 58 or 60 to alter the vertical height and size of collar 10. For example, as shown in FIG. 1 the unmodified size of the collar is chosen to fit large patients, while when collar 10 is reduced in size by tearing along perforated line 60 to fit medium sized patients. In tearing along perforated line 58, collar 10 then becomes sized to fit small sized victims. Although the illustrated embodiment has been shown in three sizes, the number of perforated lines 58 and 60 may be increased or decreased to provide a larger number of size variations.

No tools are required to tear along the perforations which can easily be accomplished by grasping peripheral portions of collar 10 with one hand on one side of perforation 58 or 60 and on the other side of the same perforation with the other hand.

Also as stated above, although perforation 58 and 60 are shown only along the bottom edge of collar 10 of FIG. 1, it is expressly within the contemplation of the invention that perforations along top edge 16 of collar 10 could be included as depicted in the second embodiment of FIG. 5. Size adjustment is then made by selectively tearing along the perforations along the top edge or bottom of collar 10 or both.

Turn now to the second embodiment of extrication collar 10 as shown in FIG. 5. FIG. 5 is a plan elevational view of collar 10 shown when laid out flatly in a single plane. FIG. 5 illustrates the exterior surface. In the illustration of FIG. 5 second foam layer 14 has been omitted, but may be included in the manner as described in connection with the embodiment of FIGS. 1–4. Collar 10 in FIG. 5 is substantially identical to collar 10 of FIG. 1 with the exception that the solid chin support 46 is not present in the embodiment of FIG. 5. In other words, front portion 18 of collar 10 is fabricated from a single flat, die-cut layer. Collar 10 in FIG. 5 also differs from the embodiment of FIG. 1 in that an integral chin support loop 62 extends from the top peripheral edge 16 of the front portion 18 of collar 10. Loop 62 is wider at its midline 64 and gradually thins to its attachment or hinge connections 66 to the main body of front portion 18. This facilitates the bending of chin loop 62 downwardly or as shown in the illustration of FIG. 5 in a direction out of the plane of illustration toward the viewer.

Collar 10 in the second embodiment is shown in perspective view as applied to the victim 28 in FIG. 6. Chin loop 62 is folded down against the lower surface of jaw 68 of victim 28 such that its inner peripheral edge 70 is typically in contact with or comes into contact with peripheral edge 16 of front portion 18 that form neck indentation 38. This provides structural support and a mechanical stop to the forward motion or bending of loop 62. The embodiment of collar 10 in FIGS. 5 and 6 is also provided with perforated lines 58 and 60 as described in the embodiment of FIGS. 1–4 in addition to which an upper perforated line 72 is shown, which also may be utilized in the embodiment of FIGS. 1–4. In the embodiment of FIG. 5 perforated lines 72 breaks into two discontinuous segments 72a and 72b in front portion 18 so as to leave the connection of chin loop 62 integrally intact to front portion 18. In the embodiment of FIG. 1 an upper perforation line similar to line 72 would be continuous across the top edge of front portion 18.

Similarly, perforation lines 58 and 60 in the embodiment of FIG. 1 and FIG. 5 have been shown to be separable portions when defined through front portion 18 and back portion 20. In other words, perforated lines 58 and 68 are separably formed and torn away in front portions 18 and 20. Their separation occurring in the area of neck down hinge 22 of collar 10. This allows a separate size adjustment of front portion 18 from back portion 20. Further, although perforations are shown in FIGS. 1 and 5 through layer 12 to be discontinuous at hinge portion 22, it is also within the scope of the invention that perforated lines 58 and 60 may be continuous or discontinuous at hinge portion 22 through foam layer 14. Foam layer 14 may or may not be bonded to foam layer 12 underneath the area from perforated line 58 to adjacent peripheral edge 16 to allow foam layer 12 to be separately torn away leaving the soft protection of foam layer 14 leaving it intact if desired.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following claims.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the invention.

I claim:

1. A cervical collar comprising:
   a body, having a vertical height, adapted for being wrapped around a user's neck and providing immobilization of said neck; and
   at least one perforated line defined at least part way through said body and rendering at least part of said body manually separable from said body without the use of a tool, said separable portion defined along at least a portion of said body so that separation of said portion effects a change in vertical height of said body insofar as structural support for immobilization of said neck is concerned,
   whereby a single cervical collar size can be adapted to users having different neck lengths.

2. The collar of claim 1 wherein said body comprises a first substantially non-compressible flexible layer and a second compressible flexible layer affixed thereto, said first layer for providing structural support, and said second layer for providing cushioning for said user.

3. The collar of claim 2 wherein said first layer is comprised of 10 pound cross-linked polyethylene foam and said second layer comprised of 2 pound cross-linked polyethylene foam.

4. The collar of claim 2 wherein said at least one perforated line is at least partially defined through said first layer.

5. The collar of claim 4 wherein said at least one perforated line is completely defined through said first layer.

6. The collar of claim 5 wherein said at least one perforated line is at least partially defined through said second layer.

7. The collar of claim 6 wherein said at least one perforated line is completely defined through said second layer.

8. The cervical collar of claim 5 wherein said at least one perforated line is continuous.

9. The cervical collar of claim 5 wherein said at least one perforated line is discontinuous.

10. The cervical collar of claim 4 wherein said at least one perforated line is continuous.

11. The cervical collar of claim 4 wherein said at least one perforated line is discontinuous.

12. The collar of claim 2 wherein said body has an upper and lower periphery and wherein said second layer is not affixed to said first layer at least between the closest one of said upper and lower peripheries and at least one perforated line.

13. The cervical collar of claim 1 wherein said body has an upper peripheral edge and a lower peripheral edge and wherein said at least one perforated line is defined adjacent to said lower peripheral edge.

14. The cervical collar of claim 1 wherein said body has upper and lower peripheral edge and wherein said at least one perforated line is defined adjacent to said upper peripheral edge.

15. The cervical collar of claim 1 wherein said body has an upper and lower peripheral edge and where said perforated line is defined adjacent to both upper and lower peripheral edges.

16. The cervical collar of claim 1 wherein a plurality of perforated lines are defined through said body, each perforated line defining a size of said body for the different size of user.

17. The cervical collar of claim 1 wherein said at least one perforated line is continuous.

18. The cervical collar of claim 1 wherein said at least one perforated line is discontinuous.

19. The collar of claim 1 wherein said body further comprises a jaw support extending from said body.

20. The collar of claim 19 wherein said jaw support is a jaw loop integrally connected to said body and hinged thereto.

21. A cervical collar comprising:
   a body, having an upper and a lower peripheral edge, adapted for being wrapped around a user's neck and providing immobilization of said neck; and
   at least one perforated line defined at least part way through said body adjacent to one of said peripheral edges and rendering at least part of said body manually separable from said body without the use of a tool, said separable portion defined along at least a portion of said body so that separation of said portion effects a change in size of said body insofar as structural support for immobilization of said neck is concerned,
   whereby a single cervical collar size can be adapted to users of different sizes.

22. The cervical collar of claim 21 wherein said perforated line is defined adjacent to both upper and lower peripheral edges.

* * * * *